(12) United States Patent
    Phillips

(10) Patent No.: US 12,409,295 B2
(45) Date of Patent: Sep. 9, 2025

(54) SYSTEM AND METHODS FOR PROVIDING VIBRATIONAL STIMULATION

(71) Applicant: Wave Neuroscience, Inc., Newport Beach, CA (US)

(72) Inventor: James William Phillips, Fountain Valley, CA (US)

(73) Assignee: Wave Neuroscience, Inc., Newport Beach, CA (US)

( * ) Notice: Subject to any disclaimer, the term of this patent is extended or adjusted under 35 U.S.C. 154(b) by 956 days.

(21) Appl. No.: 17/449,662

(22) Filed: Sep. 30, 2021

(65) Prior Publication Data

US 2022/0096785 A1    Mar. 31, 2022

Related U.S. Application Data

(60) Provisional application No. 63/085,570, filed on Sep. 30, 2020.

(51) Int. Cl.
    *A61M 21/00*    (2006.01)
(52) U.S. Cl.
    CPC ..... *A61M 21/00* (2013.01); *A61M 2021/0022* (2013.01); *A61M 2209/088* (2013.01); *A61M 2230/10* (2013.01)
(58) Field of Classification Search
    CPC ........... A61B 5/4806–4818; A61B 5/369–386; A61M 2230/10
    See application file for complete search history.

(56) References Cited

U.S. PATENT DOCUMENTS

| | | | |
|---|---|---|---|
| 8,456,408 B2 | 6/2013 | Chan et al. | |
| 8,475,354 B2 | 7/2013 | Phillips et al. | |
| 8,480,554 B2 | 7/2013 | Phillips et al. | |
| 8,585,568 B2 | 11/2013 | Phillips et al. | |
| 8,870,737 B2 | 10/2014 | Phillips et al. | |
| 8,926,490 B2 | 1/2015 | Phillips et al. | |
| 9,015,057 B2 | 4/2015 | Phillips et al. | |
| 9,308,385 B2 | 4/2016 | Jin | |
| 9,649,502 B2 | 5/2017 | Phillips et al. | |
| 9,962,555 B1 | 5/2018 | Charles et al. | |
| 10,342,986 B2 | 7/2019 | Jin | |
| 10,350,427 B2 | 7/2019 | Jin et al. | |
| 10,398,906 B2 | 9/2019 | Jin | |
| 10,420,482 B2 | 9/2019 | Jin | |
| 10,420,953 B2 | 9/2019 | Jin | |
| 11,478,606 B1* | 10/2022 | English | A61M 21/02 |
| 2013/0267759 A1* | 10/2013 | Jin | A61N 2/002 |
| | | | 600/27 |
| 2014/0357960 A1* | 12/2014 | Phillips | A61B 5/742 |
| | | | 600/545 |
| 2016/0045756 A1 | 2/2016 | Phillips et al. | |
| 2017/0296837 A1 | 10/2017 | Jin | |

(Continued)

FOREIGN PATENT DOCUMENTS

| WO | 2018136431 A1 | 7/2018 |
|---|---|---|
| WO | 2022073025 A1 | 4/2022 |

OTHER PUBLICATIONS

International Search Report and Written Opinion, mailed Feb. 7, 2022, for International Application Serial No. PCT/US2021/071669 filed Sep. 30, 2021.

*Primary Examiner* — Thaddeus B Cox
(74) *Attorney, Agent, or Firm* — K&L Gates LLP

(57) ABSTRACT

System and methods are described herein for providing vibrational energy to a user.

19 Claims, 4 Drawing Sheets

(56) References Cited

U.S. PATENT DOCUMENTS

| | | | |
|---|---|---|---|
| 2018/0055402 A1* | 3/2018 | Izvarina | A61B 5/375 |
| 2018/0104504 A1 | 4/2018 | Jin et al. | |
| 2018/0229049 A1 | 8/2018 | Phillips et al. | |
| 2019/0070428 A1* | 3/2019 | Phillips | A61N 2/02 |
| 2020/0114116 A1 | 4/2020 | Dubey et al. | |

* cited by examiner ns of the brain regions of the transcended by the patient. This patent is one of the is described in the following detailed description:

SYSTEM AND METHODS FOR PROVIDING VIBRATIONAL STIMULATION

PRIORITY

This application claims priority to U.S. Provisional Patent Application No. 63/085,570, filed Sep. 30, 2020 and is incorporated by reference in its entirety herein.

BACKGROUND

Described herein are methods and systems for novel, inexpensive, easy to use therapy for a number of mental disorders. Research has shown that energy imparted to the brain of a person may bring about changes in functionality, due to the brain's natural neuroplasticity. Repetitive Transcranial Magnetic Stimulation (rTMS) imparts energy to the brain using high energy electromagnetic pulses delivered by a coil placed near the person's scalp. When directed at a target region of the brain, changes in the characteristics of neuronal firing beneath the coil can be brought about. However, if the magnetic pulses are provided at an intrinsic frequency of an EEG band of the person, the energy of the magnetic pulses may be decreased significantly, while still bringing about the desired changes. This is due to the natural resonance of the brain at its intrinsic frequency.

The functional changes to the brain's neuronal activity as a result of stimulation at the brain's intrinsic frequency is that the brain becomes "tuned", in that neuronal firings across the brain become more rhythmic, synchronous, and coherent. The increased brain synchronicity improves the person's focus, concentration, calmness, and may also improve the symptoms of a large number of mental disorders. When the brain is tuned, the EEG around the bandwidth of the intrinsic frequency distribution of a specified EEG band tends to narrow, resulting in an increased Q-factor. The Q-factor is defined as the ratio of the intrinsic frequency divided by the bandwidth of the frequency distribution about the intrinsic frequency. It is also possible to de-tune the brain of the person by imparting stimulation that is not at the brain's intrinsic frequency, resulting in a decreased Q-factor. For example, the stimulation frequency could be greater than 1 Hz away from the brain's intrinsic frequency. In another example, the stimulation frequency could shift randomly at periodic intervals to values that are not equal to the brain's intrinsic frequency.

If the frequency of stimulation is set to a value that is different from the intrinsic frequency, but within about ½ Hz from the intrinsic frequency, the stimulation energy tends to "pull" the intrinsic frequency toward the frequency of stimulation. Therefore, it is also possible to change the intrinsic frequency toward a pre-specified target value.

If the frequency of stimulation is such that a significant portion of the head is affected, the energy will affect multiple regions of the brain, making the neuronal firing more coherent between physically separate brain regions. Therefore, it is also possible to change the coherence toward a pre-specified target value.

Since the energy of stimulation may be lowered when the frequency content of the energy is set to the person's intrinsic frequency, other lower energy modalities may be used, and still achieve an effect. For example, transcranial Alternating Current Stimulation (tACS) uses electrodes on the scalp, which provide very low energy electrical pulses to the brain of the person through the skull, and if those electrical pulses are targeting the brain's intrinsic frequency of neuronal firing, then a change in brain functionality can be brought about, even though the stimulation is very low.

Examples of energy stimulation may be found in, for example, U.S. Pat. Nos. 8,456,408; 8,475,354; 8,480,554; 8,585,568; 8,870,737; 8,926,490; 9,015,057; 9,308,385; 9,649,502; 9,962,555; 10,342,986; 10,350,427; 10,398,906; 10,420,482; and 10,420,953; and US Publication Nos. 2016/0045756; 2017/0296837; 2018/0104504; and 2018/0229049, each of which is incorporated by reference in their entirety herein.

SUMMARY

Exemplary embodiments described herein include systems and methods of applying vibrational energy to the head of a subject.

Exemplary embodiments described herein include systems and methods of adjusting a vibrational energy source for influencing an intrinsic frequency of a specified EEG band of a subject toward a pre-selected or target intrinsic frequency of the specified band and applying the vibrational energy to the head of a subject. Other EEG based influences may also or alternatively be made. For example, harmonics and/or sub-harmonics of the intrinsic frequency may be used. The vibrational energy source may also or alternatively be used to influence a Q-factor, EEG phase, and/or coherence of intrinsic frequencies among multiple sites in a brain, and any combination thereof.

In an exemplary embodiment, the vibrational energy may be created by rotating and/or translating weights. The weights may be magnetic.

In an exemplary embodiment, the vibrational energy is applied in conjunction with a magnetic and/or electric stimulation at a frequency. The frequency of the electric and/or magnetic stimulation may be approximately equal to, a harmonic of, and/or subharmonic of the frequency of the vibrational stimulation.

DRAWINGS

DESCRIPTION

Figure 1:
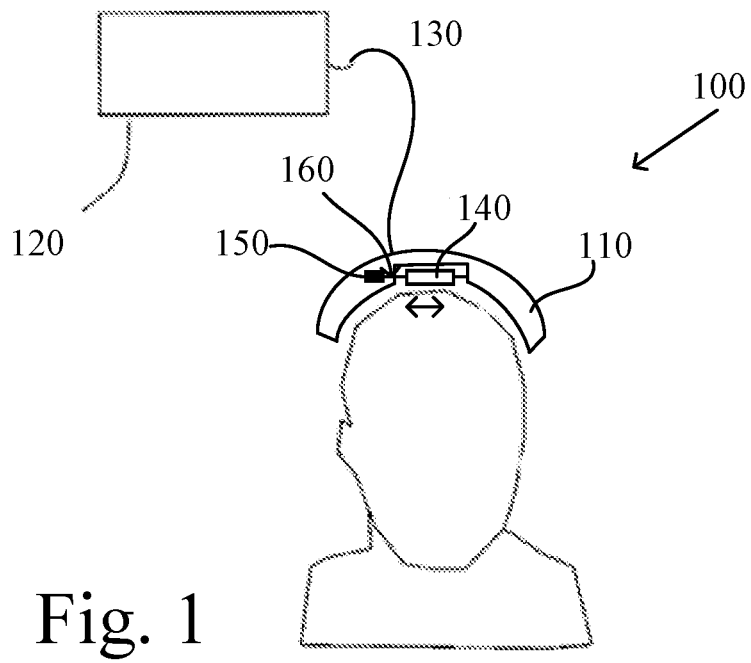
FIG. 1 illustrates an exemplary device and partial component views of a device according to embodiments of the invention.

The following detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. It should be understood that the drawings are diagrammatic and schematic representations of exemplary embodiments of the invention, and are not limiting of the present invention nor are they necessarily drawn to scale.

It is possible to impart very low magnetic energy to the brain using moving magnets, and still bring about changes in neuronal functionality, when the magnets are moved at a frequency which matches, or is a harmonic or subharmonic of the brain's intrinsic frequency of neuronal firing.

Although embodiments of the invention may be described and illustrated herein in terms of applying vibrational energy to the head of a patient, it should be understood that embodiments of this invention are not so limited, but are additionally applicable to applying vibrational energy to other locations of the body. Furthermore, although embodiments of the invention may be described and illustrated herein in terms of a patient, it is understood that the subject may be any living target, including mammalian targets of animals and/or humans.

Physical vibration is a form of energy, which comprises a stimulation frequency. Some examples of mechanical vibration include a tuning fork, a pendulum, quartz crystal, or the sound waves produced when a tone is produced by a person or musical instrument. Such vibration, when generated at a specific frequency, can have significant effects on an object that has a resonant frequency. For example, an opera singer may shatter a crystal glass when their pitch matches the resonant frequency of the glass. In another example, the Tacoma Narrows Bridge collapsed in 1940 when a rhythmic breeze matched the resonant frequency of the bridge.

When a physical vibration is applied to the head of a person, that vibrational energy is applied to the person's brain. The vibration produces minute fluctuations in localized intracranial pressure. This pressure variation affects neuronal depolarization thresholds and cellular excitability. The magnitude of the energy imparted through vibration is similar to that produced by a low-level magnetic field at the same frequency.

The vibration may be applied externally, using a vibrating headset or other device(s), or internally, using an implanted vibrational mechanism. The vibration could be linear, where the head is vibrated along a single vector. For example, a vibration device could move the head forward and backward. In another example, the vibration device could move the head side to side. In another example, the vibration device could move the head up and down. In another example, the vibration device could move the head inward and outward, essentially along a radial length from the surface of the head. The directional orientation is for reference only and is taken through the head of the patient, with "up" being out of the top of the head of the patient and forward being outward in front of the patient's face. The directional queues are intended to be general only, and may include variations from the contours of the patient's head. The vibration could also be rotational, where the head is rotated slightly clockwise or counterclockwise.

In an exemplary embodiment, the applied vibrational energy may be pulsed, such that the headset or other device(s) only moves in a pulsed fashion, imparting similar pulsed energy to the brain. The vibration could be sinusoidal, where the headset or other device(s) moves in an oscillating fashion.

In one aspect are methods of treating a subject comprising: (a) adjusting the vibration of a vibrating surface for influencing Q-factor, a measure of frequency selectivity and rhythmicity of a specified EEG band, of the person toward a pre-selected or target Q-factor of the band; and (b) applying said vibrating surface to the head of the subject.

In another aspect are methods of treating a subject comprising: (a) determining the Q-factor of the intrinsic frequency within the specified EEG band of the subject; (b) comparing the Q-factor of the intrinsic frequency from step (a) to an average Q-factor of the intrinsic frequency of a healthy population database. If the Q-factor of the intrinsic frequency from step (a) is higher than the average Q-factor of the intrinsic frequency of a healthy population database, tuning down the Q-factor of the intrinsic frequency of the subject by applying a vibrating surface with a plurality of vibration frequencies or with a single pre-selected vibration frequency close to a head of the subject; and if the Q-factor of the intrinsic frequency from step (a) is lower than the average Q-factor of the intrinsic frequency of the healthy population database, tuning up the Q-factor of the intrinsic frequency of the subject by applying vibrating surface to the head of the subject with a pre-selected vibration frequency.

The vibrations may be generated by many different methods, and/or devices, and/or combinations thereof. For example, vibration may be linear, in which a weight is moved back and forth. The linear vibration could be parallel to the head, moving from front to back. The linear vibration could be parallel to the head, moving from side to side. The linear vibration could be perpendicular to the head, moving up and down. The linear vibration could be radial, moving toward the head and then away from the head. When multiple linear vibrations are applied at the same time synchronously, the resulting vibration is a vector that is the sum of the vectors of the linear vibrations. Therefore, it is possible, using multiple vibrating weights, to vibrate the head in any vector desired.

The vibration may be rotational. For example, a weighted cylinder may be rotated above the person's head, where the cylinder rotates back and forth, rotating for only a brief period in any one direction, before changing direction. The rotational vibration may be at any angle relative to the person's head. The rotational weight may be symmetric and rotated about an axis of symmetry. The rotational weight may also by asymmetric or symmetric and rotated off axis.

The vibration could be caused by the push and pull of magnets toward each other. For example, if diametrically magnetized cylindrical magnets are rotated near each other, they will exert a pulling and pushing force on each other, depending on the orientation of the magnetic poles. The closer the magnets are to each other, the greater the force. If one or both of the magnets are affixed to the vibration surface using a spring or other flexible material, the magnets will shift back and forth as they rotate, and the moving mass of the magnets will result in vibration. A similar vibration may result by a single magnet and a ferrous metal object, such as a lead slug. If the magnet or the slug is affixed to the vibration surface using a spring or other flexible material, then the magnet and/or the slug will shift back and forth as the magnet is rotated, and the moving mass of the magnet and/or the slug will result in vibration.

A vibration system may comprise a headset that fits comfortably on a person's head. The headset may include a surface configured to vibrate. The headset may be configured to be worn so that the vibrating surface is in close proximity and/or in contact with the person's head. As used herein, close proximity is understood to include direct contact with a person's head and/or sufficiently close to a person's head such that the vibrational energy is transferred to the person's head and/or brain.

In an exemplary embodiment, the vibration system and headset includes a moving element that is configured to move, either translationally (in one or more directions) and/or rotationally. The moving element may be configured to impart a vibration on to the vibrational surface. For example, the moving element may be coupled to the vibrating surface through a spring or flexible material. The moving element may be coupled to the headset, such as on an axis or rod to permit translational and/or rotational movement along or about the axis.

In an exemplary embodiment, the system and method may include a moving element. The movement may be used to generate vibrational energy. The vibrational energy may be continuously applied. The vibrational energy may be provided in pulses.

Exemplary embodiments of a system may include EEG recording device, in order to detect the intrinsic frequency of an EEG band. Such a system may use the intrinsic frequency of the EEG band to specify the vibration frequency for the system. The EEG may be recorded before a treatment session or it may be recorded during a treatment session. It is also possible to pause the vibration for a short period to allow an EEG to be recorded. The vibration frequency may be updated based upon the most recently recorded EEG.

The system may record an EEG, and then transmit the EEG to a handheld device running an application, and the application could determine the optimal vibration frequency, and transmit that frequency back to the system. This would allow the application on the handheld device to be updated if the algorithm to determine the intrinsic frequency or the optimal vibration frequency changes. It would also allow the storage of EEG files in order to generate a report or to track changes to the EEG resulting from the vibration treatment.

The system may record an EEG, and then transmit the EEG to an external system which communicates with a remote server, and a program on the server could determine the optimal vibration frequency, and send that frequency back to the external system, which transmits the frequency to the vibration system. This would allow the software on the server to be updated if the algorithm to determine the intrinsic frequency or the optimal vibration frequency changes. It would also allow the storage of EEG files in order to generate a report or to track changes to the EEG resulting from the vibration treatment.

FIG. 1 shows an exemplary drawing of a vibration system 100 in which a weight 140 moves from side to side above a person's head, and the weight 140 is incorporated into a wearable headset 110 worn by the person. The frequency of movement of the weight 140 is equal to the optimal vibration frequency. The weight 140 in the figure is attached to a shaft 160, and the weight 140 moves along that shaft 160. Alternately, the weight 140 could be attached to a cable 130, and the cable 130 is moved from side to side in the headset 110. The vibration system 100 may also include a motor 150 in order to rotate and/or translate the weight 140 according to embodiments described herein. The system 100 may also include a controller 120 for receiving control instructions from the user and/or to provide control commands for the system described herein.

Figure 2:
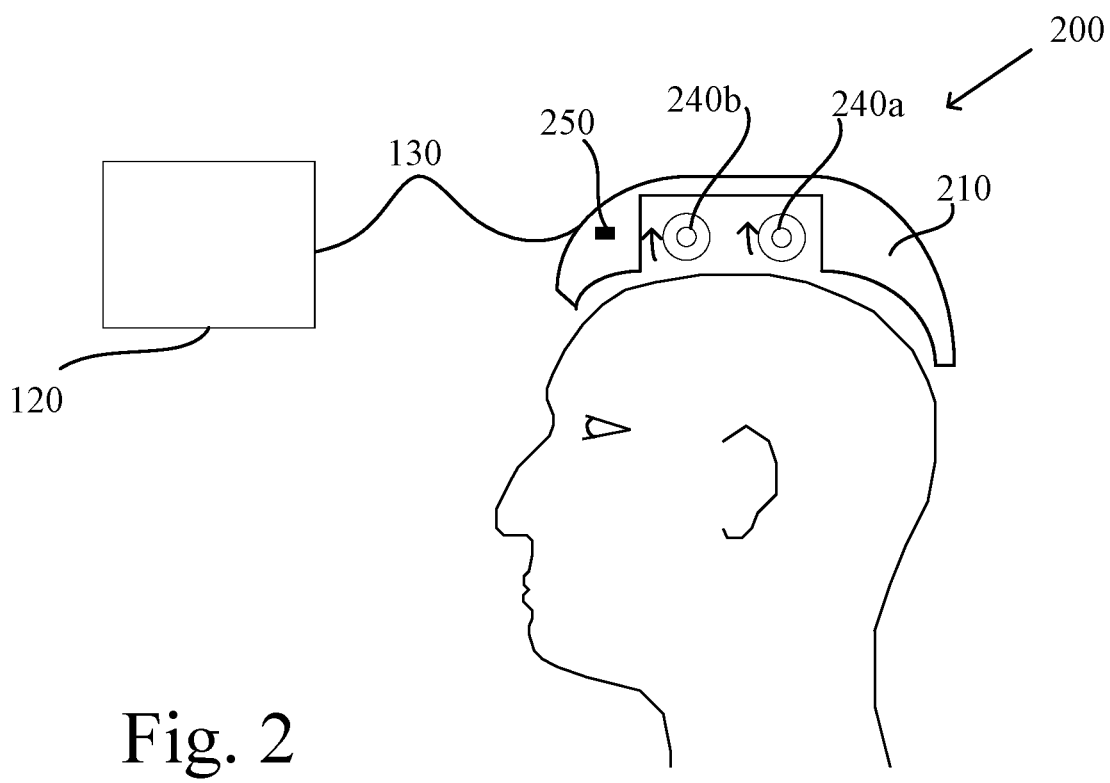
FIG. 2 illustrates an exemplary device and partial component views of a device according to embodiments of the invention.

FIG. 2 shows an exemplary drawing of a vibration system 200 in which two diametrically magnetized cylindrical magnets 240a and 240b are rotated above a person's head. The magnets 240a and 240b could be mounted to a headset 210 that is worn by the person. The magnets 240a and 240b could be rotated using a motor 250. It is also possible to rotate only one magnet 240a or 240b with the motor 250, and the other magnet 240a or 240b will rotate on its own due to the attraction and repulsion due to the magnetic fields generated by the magnets 240a or 240b. If the magnets 240a and 240b are mounted on shafts, the shafts and motors 250 could be mounted to the headset 210 using a spring or other flexible material, which would allow the magnets 240a and 240b and motors 250 to shift during rotation, resulting in vibration. The system 200 may also include a controller 120 coupled to the headset 210 through a wired or wireless connection 130.

Figure 3:
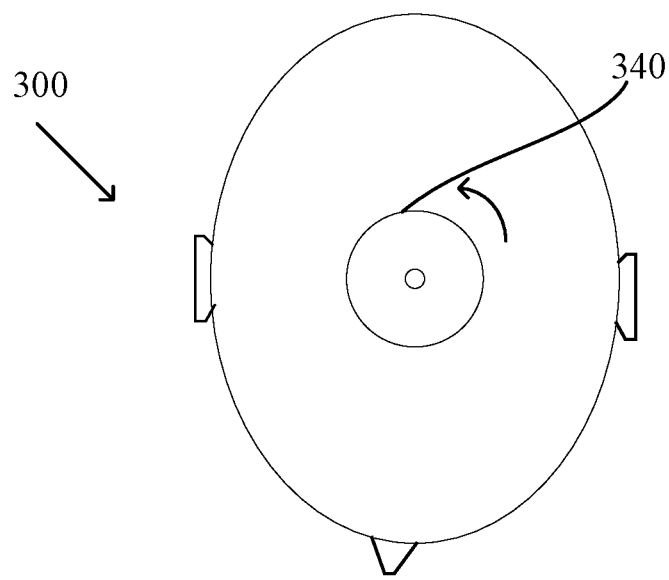
FIG. 3 illustrate an exemplary device and partial component views of a device according to embodiments of the invention.

FIG. 3 shows an exemplary drawing of a vibration system 300 in which a weighted cylinder 340 is rotated back and forth. The rotating cylinder 340 is mounted to a headset worn by the person. Since the cylinder 340 has weight, the momentum will result in a rotational vibration. The rotational movement of the cylinder 340 may be performed using a motor that moves clockwise and counterclockwise alternately. The headset in this exemplary embodiment is removed for illustration purposes.

Figure 4:
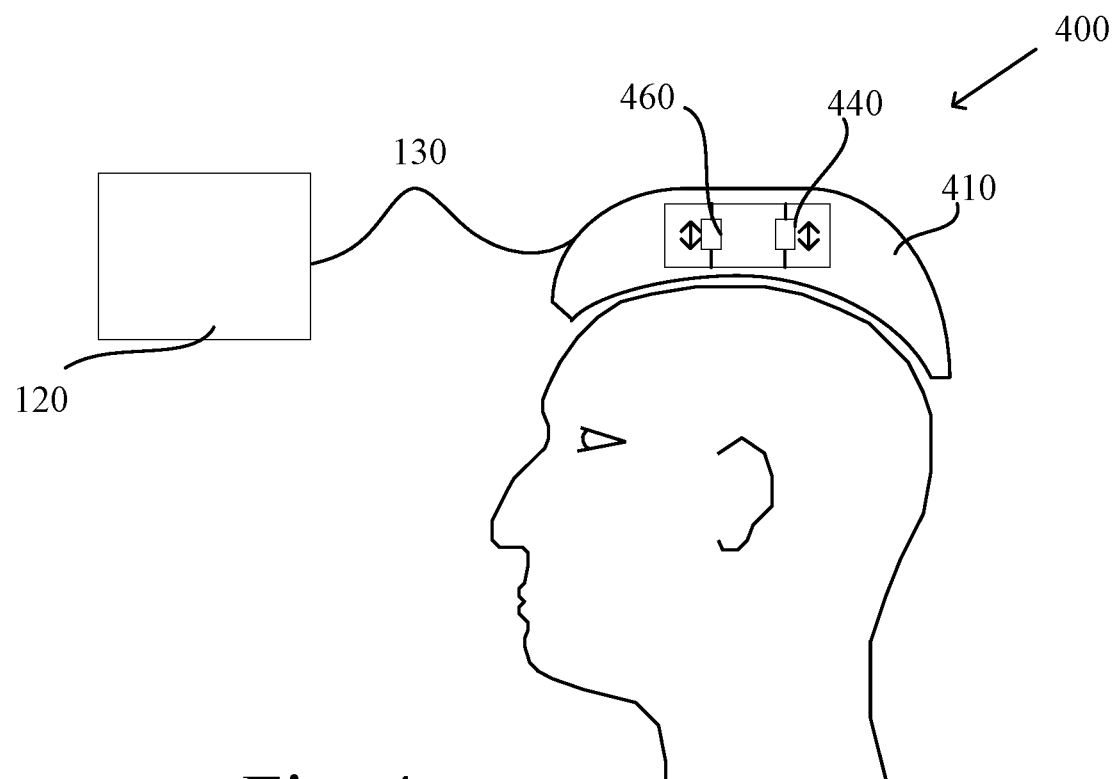
FIG. 4 illustrate an exemplary device and partial component views of a device according to embodiments of the invention.

FIG. 4 shows an exemplary drawing of a vibration system 400 in which two weights 440 and 460 move linearly alternately toward and away from the person's head. In this drawing, two weights 440 and 460 are included. Preferably, the weights 440 and 460 would by synchronous and in phase, resulting in an additive effect, resulting in greater vibration. Weights 440 and 460 may be moved along shafts, or may be part of cables 130 that are moved alternately toward and away from the person's head. The moving weights 440 and 460 may be mounted in a headset 410 that is worn by the person.

Figure 5:
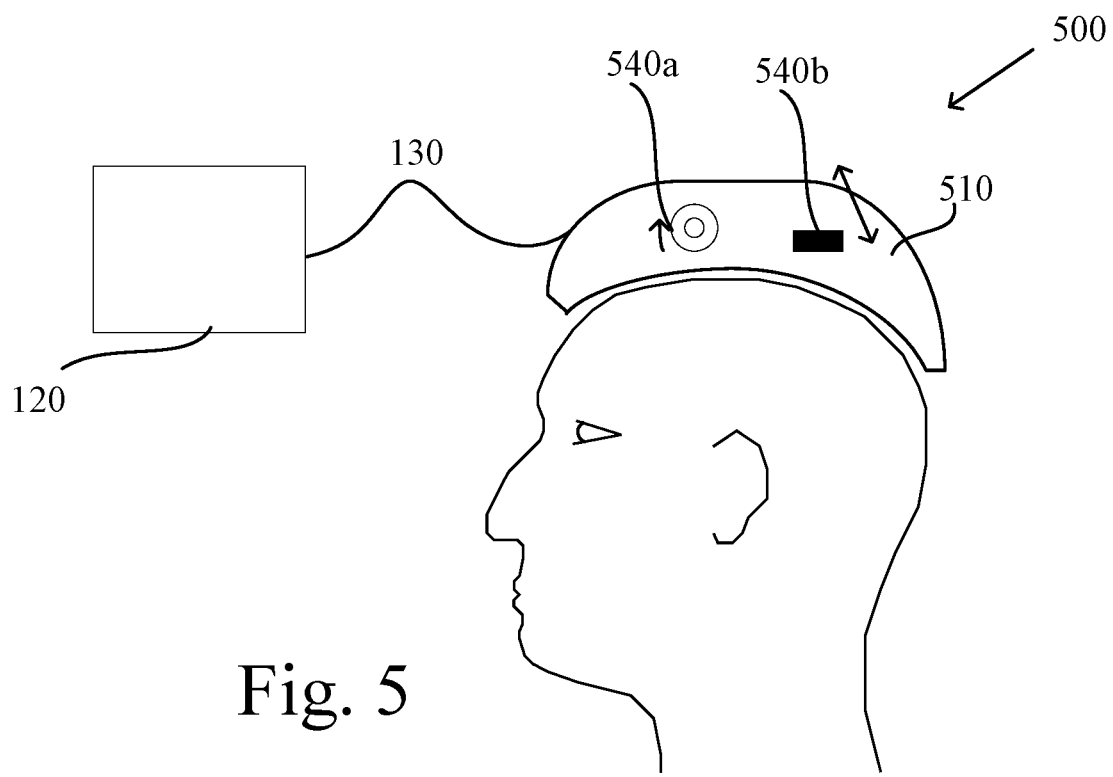
FIG. 5 illustrates an exemplary device and partial component views of a device according to embodiments of the invention.

FIG. 5 shows an exemplary drawing of a vibration system 500 in which a single diametrically magnetized cylindrical magnet 540a is rotated near a slug 540b made from a ferrous material. The rotating permanent magnet 540a exerts a push and pull force on the slug 540b, depending on the position of the north and south poles on the rotating magnet 540a. The magnet 540a and slug 540b may be mounted to a headset 510 which is worn by the person. If the magnet 540a and slug 540b are mounted to the headset 510 using a spring or other flexible material, the magnet 540a or slug 540b may shift position during rotation, resulting in vibration.

Figure 6:
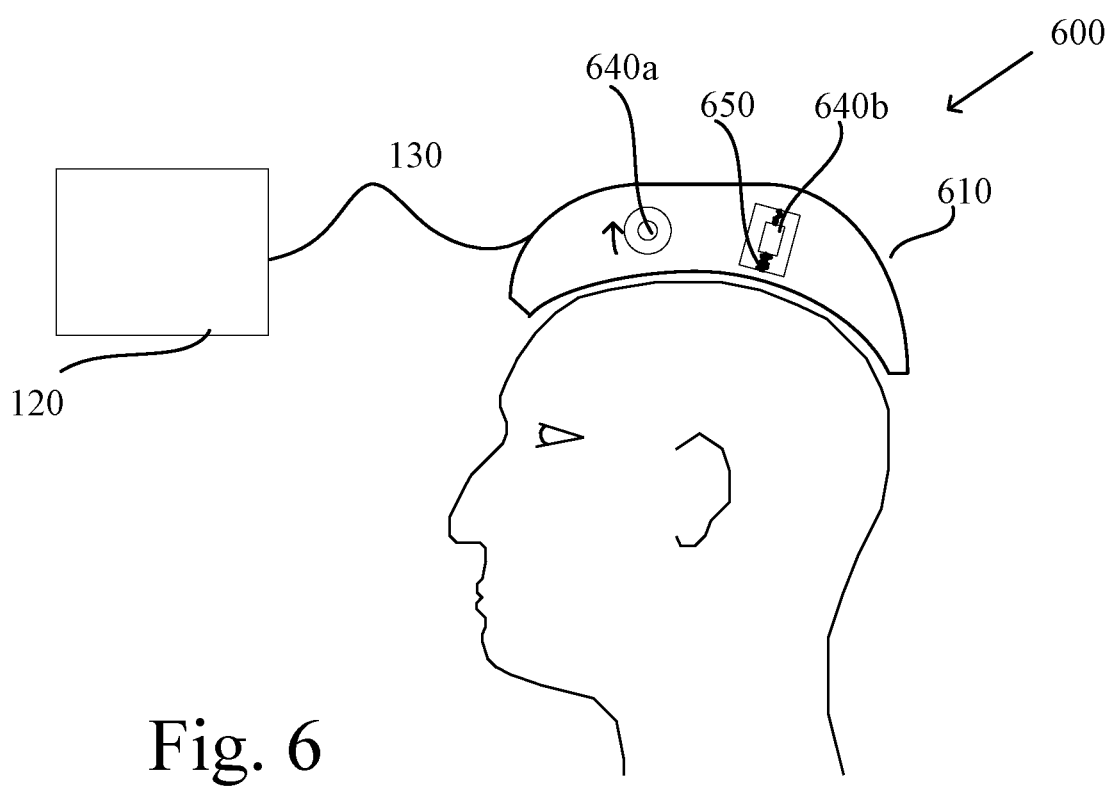
FIG. 6 illustrates an exemplary device and partial component views of a device according to embodiments of the invention.

FIG. 6 shows an exemplary drawing of a vibration system 600 in which a diametrically magnetized cylindrical magnet 640a is rotated near a fixed magnet 640b. The fixed magnet 640b may be oriented so that either the north or south pole is closest to the rotating magnet 640a. The rotating magnet 640a and fixed magnet 640b exert a push and pull force on each other, depending on the location of the north and south poles of the rotating magnet 640a. The two magnets 640a and 640b may be mounted to a headset 610 which is worn by the person. If one or both of the magnets are mounted to the headset 610 using a spring 650 or other flexible material, the magnets 640a and 640b may shift position during rotation, resulting in vibration.

Figure 7:
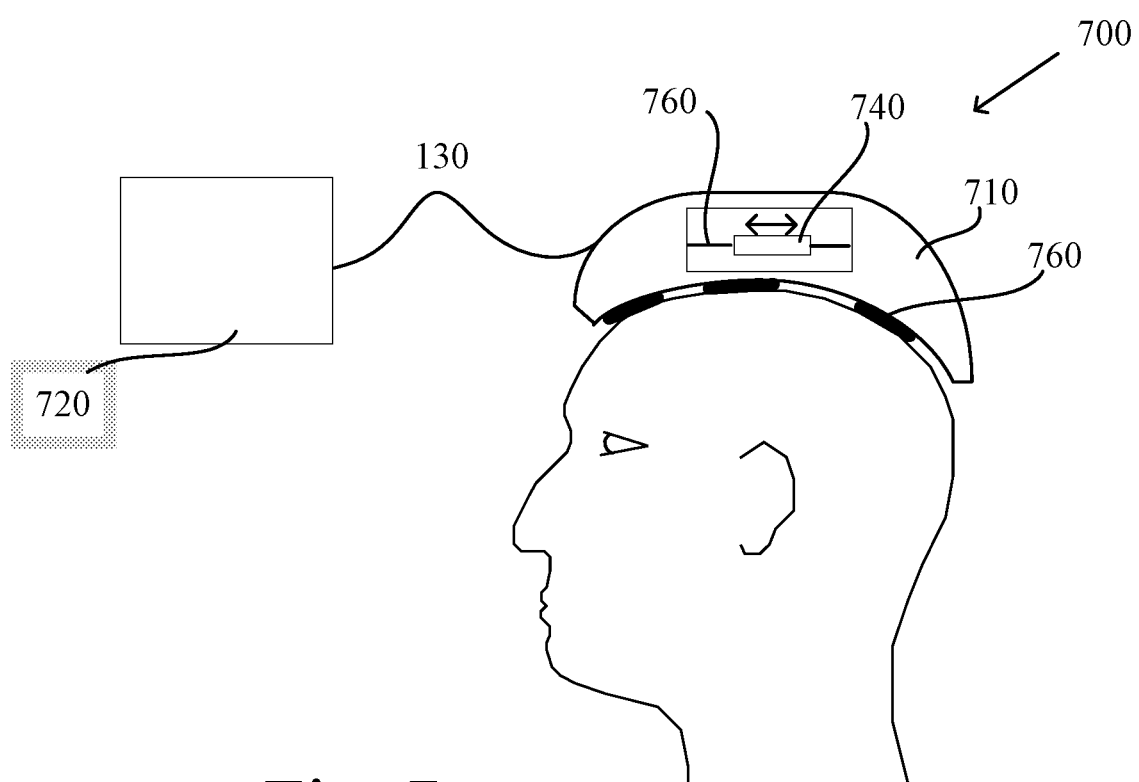
FIG. 7 illustrates an exemplary device and partial component view according to embodiments of the invention.

FIG. 7 shows an exemplary drawing of a vibration system 700 in which a weight 740 is moved back and forth near a person's head. The moving weight 740 may be mounted to a headset 710 which is worn by the person. The headset 710 may comprise electrodes 760, which are used to record the EEG of the person. Logic may be included in the headset 710 or a console 720 to record the person's EEG, and to determine the intrinsic frequency of an EEG band, and to determine the optimal vibration setting. Alternately, the headset 710 may be configured to communicate with a handheld device running an application, and the calculation may be performed in the handheld device. Alternately, the headset 710 may be configured to communicate with a remote server, and the calculation may be performed on the server and sent back to the vibration system. The headset may therefore have a communication device such as for wired or wireless communication to the desired object for processing and/or upload and/or download of information, data, and/or software.

Any exemplary embodiment described herein may take advantage of any combination of features provided herein. Therefore, any figure is exemplary only and may be combined with any other combination of features, such as the spring support, use of different combinations of magnets, weights, slugs, controllers, electrodes, consoles, wires, etc. Each component may be duplicated, added, removed, subdivided, or otherwise recombined and remain within the scope of the instant disclosure.

The vibration system may be combined with other means of brain stimulation. For example, the vibration system may be combined with a coil-based rTMS system, resulting in additive benefit. The rTMS system may be programmed to provide stimulation with a pulse frequency that matches the vibration frequency. If rotating magnets are used to provide magnetic stimulation, the magnets could be mounted so that they produce vibration along with generation of the magnetic field. This may produce an additive effect for the person. Vibration could be combined with electrical stimulation, such as tDCS or tACS, for additive effect. This is especially true if the tACS pulse frequency matches the vibration frequency.

In some embodiments of at least one aspect described above, the step of applying the vibrational energy, magnetic energy, and/or electric energy is at an intrinsic frequency, harmonic, and/or subharmonic of the intrinsic frequency of an EEG band. The intrinsic frequency within the specified EEG band may be from about 0.5 Hz to about 100 Hz. In some embodiments of at least one aspect described above, the target intrinsic frequency within the specified EEG band is not greater than about 50 Hz. In some embodiments of at least one aspect described above, the target intrinsic frequency within the specified EEG band is not greater than about 30 Hz. In some embodiments of at least one aspect described above, the target intrinsic frequency within the specified EEG band is not greater than about 20 Hz. In some embodiments of at least one aspect described above, the target intrinsic frequency within the specified EEG band is not greater than about 10 Hz. In some embodiments of at least one aspect described above, the target intrinsic frequency within the specified EEG band is greater than about 3 Hz. In some embodiments of at least one aspect described above, the target intrinsic frequency within the specified EEG band is greater than about 1 Hz. As used herein, the term about is referring to a frequency that may include some variation and/or deviation as would be understood by a person of skill in the art. For example, the devices and systems used may include normal tolerances and/or variations, which would inform a permissible and/or expected range that a device may deviate and remaining within the "about" limitation. The term about may be in reference to achieving the desired clinical result. For example, a desired target frequency may be within 0.5 Hz and still achieve the same or approximate clinical results and/or at least achieve improvement in the condition of the patient. Accordingly, above may be a range about a given number that achieves a clinical benefit as the given number, a clinical benefit that approximates or is substantially similar to the given number, and/or achieve a benefit to the patient.

In some embodiments of at least one aspect described above, the magnetic vibrational energy is generated by movement of at least one permanent magnet. In some embodiment, the movement comprises rotation of at least one permanent magnet. The movement may comprise linear motion of at least one permanent magnet. In some embodiments, the movement may include curvilinear motion of at least on permanent magnet. The movement may comprise at least one of rotational motion, linear motion, and/or swing motion.

In some embodiments of at least one aspect described above, the method improves an indication selected from the group consisting of replacement for meditation, quick nap, stress release, attention span, comprehension, memory, lowered blood pressure, increased libido, sports performance, academic performance, and any combination thereof. In some embodiments of at least one aspect described above, the method improves a mental disorder selected from the group consisting of depression, bipolar, anxiety, obsessive-compulsive, seizure, Parkinson's disease, ADHD, autism, substance abuse, head injury, Alzheimer's disease, eating disorder, sleep disorder, tinnitus, and any combination thereof. In some embodiments of at least one aspect described above, the method improves symptoms of fibromyalgia. In some embodiments of at least one aspect described above, the method halts the onset of a seizure. In some embodiments of at least one aspect described above, the method prevents the onset of a seizure. In some embodiments of at least one aspect described above, the method improves a characteristic selected from the group consisting of peripheral visual response, attention span, immediate reaction time (IRT), movement time (MT), simple perceptual reaction time (SPR), conflict perceptual reaction time (CPR), and any combination thereof. In some embodiments of at least one aspect described above, the method provides an improvement as measured using a rating scale selected from the group consisting of HAMA, HAJVID, PANSS, MADRS, BARS, SAS, and any combination thereof. In some embodiments of at least one aspect described above, the method provides an improvement as measured using the Unified Parkinson's Rating Scale. In some embodiments of at least one aspect described above, the method provides an improvement as measured using a modified Unified Parkinson's Rating Scale. In some embodiments of at least one aspect described above, the method uses a Permanent Magneto-EEG Resonant Therapy (pMERT) device (alternatively called a Neuro-EEG Synchronization Therapy (NEST) device). In some embodiments of at least one aspect described above, the method does not use a Transcranial Magnetic Stimulation (TMS) device.

Exemplary embodiments may include a device further comprising logic that controls the frequency and/or activation and/or movement of the vibrational energy and/or moving component(s). In an exemplary embodiment, the frequency is controlled between about 2 and about 20 Hz in increments of about 0.1 Hz. In some embodiments of at least one aspect described herein, the device further comprises logic that controls the frequency to be any frequency between about 2 and about 50 Hz in increments of about 0.1 Hz. In some embodiments of at least one aspect described herein, the device further comprises logic that changes the frequency in response to an EEG reading of a subject before, after, and/or during treatment. In at least one aspect described herein, the device further comprises logic that allows a user to set a frequency or treatment protocol including any combination of a duration of treatment, pulse length, pulse frequency, vibrational frequency, and combinations thereof. In at least one aspect described herein, the device further comprises logic that allows a user to set a duration of a treatment before the treatment. Exemplary embodiments of the device including logic may be with a memory and process or for storing and executing the logic local to or within a housing of the machine. Exemplary embodiments of the device including logic may be with a memory and processor for storing and executing the logic local in wired and/or wireless communication with the machine. For example, logic may be on a remote server and/or handheld device of the user. Any combination of logic in different locations of the system are within the scope of the instant disclosure.

Exemplary embodiments of the system described herein can be based in software and/or hardware. While some specific embodiments of the invention have been shown the invention is not to be limited to these embodiments. For example, most functions performed by electronic hardware components may be duplicated by software emulation. Thus, a software program written to accomplish those same functions may emulate the functionality of the hardware components in input-output circuitry. The invention is to be understood as not limited by the specific embodiments described herein, but only by scope of the appended claims.

Although embodiments of this invention have been fully described with reference to the accompanying drawings, it is to be noted that various changes and modifications will become apparent to those skilled in the art. Such changes and modifications are to be understood as being included within the scope of embodiments of this invention as defined by the appended claims. Specifically, exemplary components are described herein. Any combination of these components may be used in any combination. For example, any component, feature, step or part may be integrated, separated, sub-divided, removed, duplicated, added, or used in any combination and remain within the scope of the present disclosure. Embodiments are exemplary only, and provide an illustrative combination of features, but are not limited thereto.

When used in this specification and claims, the terms "comprises" and "comprising" and variations thereof mean that the specified features, steps or integers are included. The terms are not to be interpreted to exclude the presence of other features, steps or components.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilised for realising the invention in diverse forms thereof.

The invention claimed is:

1. A device comprising:
a vibrating surface operable to be in close proximity to a head of a subject; and
a vibrational energy source coupled to the vibrating surface,
wherein the vibrational energy source is operable to generate one or more vibration frequencies at the vibrating surface to influence one or more of
a Q-factor of an electroencephalogram (EEG) band toward a target Q-factor of the EEG band,
an intrinsic frequency of the EEG band toward a target intrinsic frequency of the EEG band,
at least one of a harmonic or subharmonic of the intrinsic frequency of the EEG band toward the target intrinsic frequency of the EEG band,
an EEG phase of the intrinsic frequency of the EEG band toward the target intrinsic frequency of the EEG band, and
a coherence of: the intrinsic frequency from a first brain site, and an additional intrinsic frequency from a different brain site toward a target coherence.

2. The device of claim 1, wherein the vibrational energy source comprises:
one or more weights operable to generate the one or more vibration frequencies using one or more of linear movement or rotational movement.

3. The device of claim 1, wherein the vibrational energy source comprises:
a first weight operable to move one or more of linearly or rotationally; and
a second weight operable to move one or more of linearly or rotationally,
wherein the first weight and the second weight are operable to one or more of
move linearly in one or more of: synchronously or in-phase, and
move rotationally in one or more of: synchronously or in-phase.

4. The device of claim 1, wherein the vibrational energy source comprises:
one or more magnets operable to generate the one or more vibration frequencies using rotational movement.

5. The device of claim 1, further comprising:
one or more electrodes operable to record an EEG; and
a processor operable to
compute an EEG-based parameter based on the EEG, and
compute the one or more vibration frequencies based on the EEG-based parameter.

6. The device of claim 1, further comprising:
a communication device operable to
transmit an EEG to one or more of a handheld device or a remote server, and
receive an EEG-based parameter from the one or more of the handheld device of the remote server.

7. The device of claim 1, further comprising:
an additional stimulation source comprising one or more of an electrical stimulation source or a magnetic stimulation source,
wherein the additional stimulation source is operable to emit a pulse frequency that matches at least one of the one or more vibration frequencies.

8. The device of claim 1, wherein the vibrating surface comprises a headset.

9. A device comprising:
one or more electrodes operable to record an electroencephalogram (EEG) of a subject;
a processor operable to
compute an EEG-based parameter including one or more of: a Q-factor, an intrinsic frequency, a harmonic of the intrinsic frequency, a subharmonic of the intrinsic frequency, an EEG phase of the intrinsic frequency, a coherence of the intrinsic frequency from a first brain site and an additional intrinsic frequency from a different brain site, and
compute a target value for the EEG-based parameter, and
a vibrational energy source coupled to a vibrational surface, wherein the vibrational energy source is operable to cause the vibrational surface to vibrate at one or more vibration frequencies to influence the EEG-based parameter toward the target value.

10. The device of claim 9, wherein the vibrational energy source comprises:
one or more weights operable to generate the one or more vibration frequencies using one or more of linear movement or rotational movement.

11. The device of claim 9, wherein the vibrational energy source comprises:
a first weight operable to move one or more of linearly or rotationally; and
a second weight operable to move one or more of linearly or rotationally,
wherein the first weight and the second weight are operable to one or more of
(a) move linearly in one or more of: synchronously or in-phase, or
(b) move rotationally in one or more of: synchronously or in-phase.

12. The device of claim 9, wherein the vibrational energy source comprises:
one or more magnets operable to generate the one or more vibration frequencies using rotational movement.

13. The device of claim 9, further comprising:
a communication device operable to transmit the EEG to one or more of a handheld device or a remote server.

14. The device of claim 9, further comprising:
an additional stimulation source comprising one or more of an electrical stimulation source or a magnetic stimulation source,
wherein the additional stimulation source is operable to emit a pulse frequency that matches at least one of the one or more vibration frequencies.

15. The device of claim 9, wherein the processor is further operable to compute the target value by:
comparing the EEG-based parameter to an average value for the EEG-based parameter of a healthy population database;
selecting, when the EEG-based parameter is higher than the average value for the EEG-based parameter of the healthy population database, the target value to tune down the EEG-based parameter; and
selecting, when the EEG-based parameter is lower than the average value for the EEG-based parameter of the healthy population database, the target value to tune up the EEG-based parameter.

16. A device comprising:
one or more electrodes operable to record an electroencephalogram (EEG) of a subject;
a communication device operable to
transmit the EEG to one or more of a handheld device or a remote server, and
receive an EEG-based parameter from the one or more of the handheld device of the remote server,
a vibrating surface operable to be in close proximity to a head of a subject; and
a vibrational energy source coupled to the vibrating surface, wherein the vibrational energy source is operable to cause the vibrating surface to vibrate based on the EEG-based parameter and the vibrational energy source comprises one or more magnets operable to generate one or more vibration frequencies using rotational movement.

17. The device of claim 16, wherein the vibrational energy source further comprises:
one or more weights operable to generate the one or more vibration frequencies using one or more of linear movement or rotational movement.

18. The device of claim 16, wherein the vibrational energy source further comprises:
a first weight operable to move one or more of linearly or rotationally; and
a second weight operable to move one or more of linearly or rotationally,
wherein the first weight and the second weight are operable to one or more of move linearly in one or more of synchronously or in-phase, and move rotationally in one or more of synchronously or in-phase.

19. The device of claim 16, further comprising:
an additional stimulation source comprising one or more of an electrical stimulation source or a magnetic stimulation source,
wherein the additional stimulation source is operable to emit a pulse frequency that matches at least one of the one or more vibration frequencies.

* * * * *